United States Patent [19]
Durante et al.

[11] Patent Number: 5,861,536
[45] Date of Patent: Jan. 19, 1999

[54] OXIDATIVE AMMINATION OF BENZENE TO ANILINE USING MOLECULAR OXYGEN AS THE TERMINAL OXIDANT

[75] Inventors: Vincent A. Durante, West Chester; Tilak P. Wijesekera, Glen Mills; Swati Karmakar, Malvern, all of Pa.

[73] Assignee: Sun Company, Inc. (R&M), Philadelphia, Pa.

[21] Appl. No.: 904,169

[22] Filed: Jul. 31, 1997

[51] Int. Cl.$^6$ ................................................. C07C 209/38
[52] U.S. Cl. ............................................................ 564/408
[58] Field of Search ............................................ 564/408

[56] References Cited

U.S. PATENT DOCUMENTS 4,031,106   6/1977   Wayne .

FOREIGN PATENT DOCUMENTS 2-115138   4/1990   Japan .

OTHER PUBLICATIONS

Heumann et. al., Progress in Chemistry, vol. 42, pp. 5350542, (1994). "Palladium Complex Catalyzed Oxidative Reactions".

de Resende et. al., Preparation of Catalysts VI—Scientific Bases for the Preparation of Heterogeneous Catalysts, pp. 1050–1067, (1995). "Synthesis and Characterization of Titanium Oxide Monolayer".

Kodama et. al., Bull. Chem. Soc. Japan., vol. 68, pp. 1627–1633, (1995). "Formation Equilibrium of a Copper-(ll)–Binuclear Complex of a New Pyridyl–Containing Tetraoxo Octaaza Macrocyclic Ligand and Its Polarographic Reduction Behavior".

*Primary Examiner*—Brian M. Burn
*Attorney, Agent, or Firm*—Stephen T. Falk

[57] ABSTRACT

The present invention comprises a process for catalytic oxidative ammination of aromatic hydrocarbons which comprising contacting aromatic feedstock with oxidant, such as molecular oxygen, under suitable reaction conditions, in the presence of a catalyst comprising three essential components: a support; transition metal; and a mono- or binucleating ligand. In one embodiment of the invention the ligand comprises at least one nitro or nitroso group. In another embodiment, the ligand comprises a multidentate, chelating binuclear compound. The process is particularly suited, for example, to the one-step conversion of benzene to aniline.

32 Claims, No Drawings

OXIDATIVE AMMINATION OF BENZENE TO ANILINE USING MOLECULAR OXYGEN AS THE TERMINAL OXIDANT

FIELD OF THE INVENTION

This invention pertains to the direct, single-step oxidative ammination of aromatic hydrocarbons, for example, the ammination of benzene to aniline, using molecular oxygen or other oxidants as terminal oxidant and to catalysts useful in such processes.

BACKGROUND OF THE INVENTION

Almost 80% of aniline consumption in the U.S. is used to produce MDI, an intermediate chemical which in turn is used to produce polyurethanes. Aniline is also used to produce rubber processing chemicals, dyes and pigments, specialty fibers, pesticides, and a variety of other materials including pharmaceuticals and photochemicals.

Direct combination of ammonia and benzene to form aniline and hydrogen is disfavored thermodynamically at reasonable temperatures and pressures leading to low equilibrium conversions for the reaction. This constraint can be overcome by conducting the process oxidatively according to equation 1, the method of our invention which we call oxidative ammination:

Equation (1)

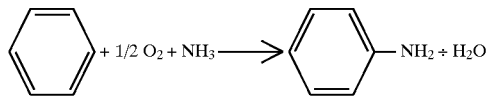

$\Delta G_{25}° = -42$ kcal/mol

All current manufacturing processes to make aniline use either nitrobenzene or phenol as the immediate precursor. Nitrobenzene is the most common feedstock for aniline; it is prepared, in turn, by a mixed acid nitration of benzene. Nitrobenzene may then be hydrogenated to aniline in high yield either in liquid or vapor phase over catalysts containing Cu, Ni, or Pt. The use of corrosive acids and environmental concerns over the acid sludges generated are major deficiencies of the process to make aniline starting from benzene.

Only one U.S. manufacturer, Aristech, used the Halcon/Scientific Design process of ammonolysis of phenol, phenol being manufactured from cumene precursor. The gas phase ammonolysis of phenol may be carried out using oxide mixtures of Mg, B, and Ti on alumina or zeolitic supports combined with cocatalysts such as V or W salts. At large excesses of ammonia, phenol conversions of up to 98% can be obtained with a selectivity to aniline about 95%.

Equations (2) and (3) describe these processes:

Equation (2) Reduction of Nitrobenzene (>85% of U.S. Capacity)

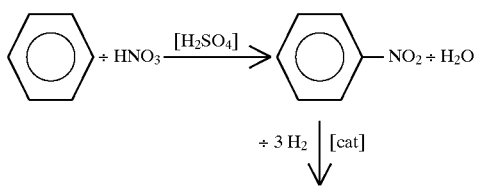

-continued

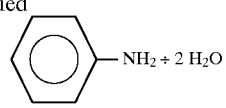

Equation (3) Ammonolysis of Phenol

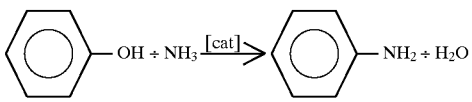

As described above, an alternative to the present invention is the production of aniline from benzene by first forming phenol, and then using known technology to convert phenol to aniline in a second step. This route is not cost competitive, in most cases, with routes through nitrobenzene intermediate to aniline from benzene, because of the high cost of phenol. However, we have found that the catalysts disclosed herein are also useful in the direct formation of phenol from benzene in one step, thereby avoiding the using cumene intermediate and facilitating a potentially cheap route to phenol. With the availability of inexpensive phenol, a cheaper route to aniline, in turn, also could be realized that might compete more effectively with the usual nitrobenzene route to aniline. An object of the present invention is to provide an alternative route through a one-step process from benzene to aniline without the need to isolate phenol as an intermediate. That process is the focus of this invention.

Competitive direct synthesis of aniline from benzene and ammonia was patented by T. W. Del Pesco of the DuPont Company [T. W. DelPesco, U.S. Pat. No. 4,031,106 (1977)]. The DuPont technology uses a Ni/NiO/ZrO$_2$ "cataloreactant" which is reduced during each run, but which can be regenerated by a separate reoxidation. Although 12% yield of aniline is realized from benzene and ammonia with this technology, 7000 psi pressure is required to conduct the synthesis. This high pressure presents a formidable barrier to commercialization.

Mitsui Toatsu researchers have reported [F. Matsuda and K. Kato, Japan Kokai J02115138-A (1990)] that by using an NH$_3$/H$_3$O mixture, it is possible to convert benzene to a mixture of phenol and aniline (1.9% yield of aniline) over a Cu$_3$(PO$_4$)$_2$/Ca$_3$(PO$_4$)$_2$ catalyst at 300°–500° C. It is not clear how much oxygen is used in this work, but the reaction appears to be equilibrium limited without oxygen addition.

A. Heumann, K. J. Jens, and M. Reglier, "Palladium Complex Catalyzed Oxidation Reactions", K. D. Karlin, ed., *Progress in Inorganic Chemistry*, 42, New York, 1994, pp. 539–541, have described Pd nitro catalysts for alkene oxidation, but not for aromatic oxidation or ammination.

An advantage of the present invention is to provide a method for the oxidative ammination of aromatic compounds which does not require the added reagent and engineering costs and operational risks associated with the use of coreductants such as hydrogen or carbon monoxide.

SUMMARY OF THE INVENTION

The present invention comprises a process for catalytic oxidative ammination of aromatic hydrocarbons which comprising contacting aromatic feedstock with oxidant, such as molecular oxygen, under suitable reaction conditions, in the presence of a catalyst comprising three essential components: a support; transition metal; and a mono- or binucleating ligand. In one embodiment of the invention the ligand comprises at least one nitro or nitroso group. In another embodiment, the ligand comprises a multidentate, chelating binuclear compound. The process is particularly suited, for example, to the one-step conversion of benzene to aniline.

DETAILED DESCRIPTION OF THE INVENTION

The present invention comprises a process for catalytic oxidative ammination of aromatic hydrocarbons which comprising contacting aromatic feedstock with ammonia and oxidant, such as molecular oxygen, under suitable reaction conditions, in the presence of a catalyst comprising three essential components: a support; transition metal; and a mono- or binucleating ligand. In one embodiment of the invention the ligand comprises at least one nitro or nitroso group. In another embodiment, the ligand comprises a multidentate, chelating binuclear compound. The process is particularly suited, for example, to the one-step conversion of benzene to aniline.

The present invention comprises a chemical process and a set of heterogeneous catalysts which enable the production of aromatic amine compounds, for example aniline, from non-activated aromatic precursors using molecular oxygen and ammonia. When using substituted aromatic compounds as feedstocks, this invention refers to catalytic oxidative amination of the ring rather than of the alkyl side chains. The present invention is also distinguished from ammoxidation processes affecting side chains. The latter produces nitrites; whereas, this invention produces predominantly amines. Hydroxy compounds such as phenol and the like also could be coproduced over the catalysts used in the process of the present invention.

The Process

The process of the present invention pertains to the oxidative ammination of aromatic feedstocks without the introduction of stoichiometric co-reductant to the system; e.g., without $H_2$ added to the $O_2$ oxidant system. This does not exclude the presence of initiators or modifiers of the catalyst which may be present in situ prior to steady-state operations; the presence of such initiators or modifiers is within the scope of the present invention.

Under some reaction conditions that are suitable for the ring ammination to occur, side chain oxidation or side chain ammination may also occur competitively. Side chain oxidation would consume a portion of the oxidant in the reactor; nevertheless, such reactions are within the scope of the present invention, provided that ring ammination also takes place. More usually, one would prefer to minimize selectivity for side chain reaction(s), and in such case, process conditions and/or catalyst components could be selected to mitigate the degree of side chain oxidations, ammination and ammoxidation.

Reaction feedstocks are typically mixtures of aromatic compounds, air, and ammonia and optionally water (steam). No particular reactor design is required and the process can be carried out in any which is suitable for vapor phase oxidation reactions. Typically, an isothermal packed bed reactor, or a continuous stirred tank reactor containing internals suitable for holding heterogeneous catalysts would be suitable. The feedstock is generally premixed and the organic: oxygen ratio usually determined by safe practices required when dealing with potentially explosive mixtures. Ammonia is usually pre-dissolved into liquid water prior to vaporization and mixing with air.

The process can be conducted over a range of reaction temperatures and pressures. The temperature may be in the range from 100° to 450° C. with a pressure greater than 0 psig. For the conversion of benzene to aniline, the temperature would preferably be in the range from 250° to 320° C. at a pressure greater than about 600 psig. Preferably, the reaction is carried out under conditions outside the explosive range for the temperature, pressure and oxygen concentrations employed.

Typically, the reaction is carried out at a temperature slightly above the critical temperature of the organic component of the feedstock. An upper limit on the temperature is generally dictated by the temperature of rapid catalyst decomposition; i.e., loss of nitro or nitroso component in the case of Pd or Ni "nitro" catalysts, or destructive loss of TOBP or other binucleating ligand in the case of V or Cu-based catalysts. At elevated temperatures, the loss of ammine ligands or other labile substituents is anticipated, but is not considered deleterious catalyst decomposition.

Suitable oxygen concentrations would comprise from 1 to 95 volume percent (vol. %) of oxygen in the gas phase at the temperature and pressure of the reaction; preferably the oxygen concentration is 5 to 50 vol. %; more preferably, 7 to 15 vol. %. To avoid explosive concentrations of oxygen, particularly in a continuous reactor, it may be desirable to pre-mix oxygen or air and steam to dilute the oxygen prior to addition of the aromatic feedstock. Suitable weight ratios of aromatic feedstock to water in the reaction process are 2000:1 to 0.2:1; preferably 1700:1 to 50:1; more preferably 1600:1 to 100:1. Preferably, the oxidant is molecular oxygen or air or other mixtures comprising $O_2$.

Suitable weight ratios of ammonia to aromatic feedstock would be about 1:1 to about 5:1. Preferably, the reaction is carried out with an excess of ammonia in the system.

The process can be conducted in different reactor configurations with either liquid phase, vapor phase, multiple liquid phase, or mixed liquid and gaseous phases of the aromatic feedstock depending on the operating parameters. Likewise, a variety of reactor types could be employed to advantage, the focus of the invention being primarily in the use of the catalysts described herein within the temperature, pressure, and oxygen concentration ranges specified herein. Suitable reactor types include, but are not limited to, packed beds, fluidized beds, slurry phase reactors, stirred tank reactors, and reactive distillation columns. Preferably, an isothermal reactor is used to carry out the process of the invention.

The Feedstocks

The aromatic feedstocks suitable for use according to the present invention may comprises unsubstituted aromatics, such as benzene and naphthalene, and compounds in which the aromatic nucleus is substituted with one or more substituents. Suitable substituted aromatic compounds may comprise aromatics substituted with one or more of the following substituents: lower alkyl groups such as methyl, ethyl, propyl, butyl; lower alkoxy groups such as methoxy, ethoxy, propoxy, etc.; halogen atoms such as chlorine, bromine, fluorine, iodine; amino and alkylamino groups; carboxyl, nitro, nitroso, sulfo, sulfone, sulfoxy groups. The foregoing list is not intended to be exhaustive and other substituents, alone or in combination with each other and/or the foregoing, may be incorporated into the feedstock ring systems so long as such substituents do not prevent ring oxidation.

The Catalysts

Two classes of catalysts have been found to be particularly useful in the process of the present invention. Among the first class of catalysts are palladium(II) or nickel(II) mononuclear or binuclear compounds which contain at least one nitro (—NO$_2$) or nitroso (—NO) group as a ligand and which are supported on a suitable support. In a preferred embodiment, the catalyst further comprises an electron-donating amido ligand in addition to the nitro or nitroso group. The solid catalysts may optionally contain about 1 to about 70% barium compounds, such as barium peroxide. A useful support is precipitated silica, but other supports are suitable as well.

Catalyst preparation technique is not critical, but incipient wetness impregnation from aqueous solution followed by drying on pre-sized supports is typical. The type catalysts of the first class include commercially available compounds. For further information on these catalysts, see A. Heumann et al., supra, the disclosure of which is hereby incorporated by reference herein.

Among the second class of catalysts useful in the process of the present invention are catalysts comprised of three essential components; namely, a support; one or more transition metal ions, selected from the group consisting of vanadium, niobium, copper, palladium, nickel and silver and combinations thereof; and an organic promoter. These catalysts are more fully described below. When used under aniline synthesis conditions as described herein, preferred catalysts of this class are V(IV) salts with TOBP promoter, supported on barium-containing solids such as Ba$^{2+}$-exchanged X-zeolite.

The catalysts useful in the process of the present invention are comprised of three essential components: a support system capable of dispersing metal complexes; at least one transition metal ion (or mixtures of several metal ions) chosen from the group consisting of vanadium, niobium, copper, palladium, nickel and silver and combinations thereof; and an organic promoter chosen from the classes of compounds described below. The organic promoter may or may not be a ligand to the metal ions. i.e., the metal ions may or may not be complexed to the promoter ligand. Additional organic or inorganic ligands in addition to the particular promoter compounds of this invention may or may not be present. Metal ion components in addition to those chosen from the set of essential metal ions also may be present. No stoichiometric co-reductant is necessary according to the process of the present invention. There is no general restriction on the method of forming the catalysts, but we have found preferred procedures and embodiments which are described below.

Catalyst supports suitable for the catalyst of the present invention preferably permit reasonable dispersion of the metal ion chosen from the set of essential metal ions, or those of its complexes that contain the promoter as a ligand, to be maintained during use. Suitable supports may consist of pure metal oxides, mixtures of metal oxides, or doped metal oxides of reasonable stability and inertness under the oxidative reaction conditions utilized in this invention. The metal oxide support may be comprised of molecular sieves, zeolites, or clays, including, for example, intercalated clays and pillared clays. Titanium framework-substituted or vanadium framework-substituted molecular sieves such as TS-1 or [V]-MCM-41 or the like can be support components, but these are not preferred. Pore structure modifications and surface treatments can be incorporated into the support system before or after incorporation of the essential metal and promoter species upon the support.

Binders and forming agents can be added to the support composites. The supports can exist in a variety of shapes and particle sizes depending on the reactor configuration to be employed and can be formed by extrusion, spray drying, tabletting, sol-gel techniques, etc. with no restriction. Supports can be shaped bodies such as monoliths, rolled corrugated sheets, cylinders, star-shaped extrudates, or more complex shapes. Burn out agents and porosity modifiers can be added and subsequently removed by calcination. The use of all of these techniques and others within the scope of the invention are within the ability of the practitioner of ordinary skill in the art.

In a preferred embodiment of the invention, at least a portion of the catalyst support comprises titanium, vanadium, magnesium, or aluminum species as a bulk component or as a surface-localized component. In a preferred embodiment of the invention, the supports comprise relatively high surface area anatase titanias of greater than 30 m$^2$/g or comprise high surface area oxides, such as aluminas of greater than 100 m$^2$/g, which have been treated with titanium- or vanadium-containing surface-active agents such that a well-dispersed overlayer containing titanium or vanadium is formed prior to the catalyst preparation step in which the metal ion component chosen from the set of essential metal ions is added. Methodology for preparing titanium oxide overlayers of this type is described in N. S. de Resende et al., *Preparation of Catalysts IV in Scientific Bases for the Preparation of Heterogeneous Catalysts*, G. Poncelet et al. (Eds.), Elsevier Science B. V., (1995), pp. 1059 if, the disclosure of which is hereby incorporated by reference herein.

The essential metal ion components of the catalyst are selected from the group consisting of vanadium, niobium, copper, palladium, nickel, and silver ions, or combinations thereof. These essential metals may be present as metal ions or related complex ions. In addition to the "essential metal ions", the catalysts useful in the present invention may further comprise additional metal ions or combinations thereof, particularly transition metals, including the Lanthanide metals; more particularly, metal ions such as cobalt (II), iron(II), iron(III), manganese, titanium (IV), ruthenium, molybdenum, tungsten, tantalum, gadolinium and combinations thereof The ratios of essential metal ion to additonal metal ion, and of essential metal ion to promoter can vary over a wide range, but preferred ranges are set forth below. Acceptable loading ranges of metal species, expressed as weight percent loading of total essential metal on a moisture-free basis on the finished solid catalyst, are in the range from 0.1 to 60 weight percent; preferably the range is from 0.5 to 10 weight percent; more preferably the range is from 1.5 to 4.5 weight percent. Molar ratios for total essential metal component (summing over all the elements of essential metal components added) to promoter compound may be in the range from about 0.1 to about 20; preferably, in the range from about 0.5 to 4; and more preferably in the range from about 0.9 to 2.5.

Metal complexes which incorporate the promoter compounds (or derivatives of promoter compounds such as deprotonated versions) as ligands may be preformed and later incorporated on a support; alternatively, the metal ions and promoter compounds can be separately added to a support. Metal ion species chosen from the set of the essential ions or non-essential additional metal ions may have an oxygen-containing species such as oxide, peroxide, superoxide, oxo, hydroxide, or water bonded to them or proximal to them in a molecular lattice structure or unit cell.

The third component of the catalysts useful in the present invention is the organic promoter which comprises a hexa-, octa- or decadentate chelating, binucleating ligand comprising heteroatom sites, and comprising at least one amido or imino group. Ligands with these components may further comprise additional features as set forth below.

Although the promoter may or may not be bonded to metal ions in the active catalyst, the structure of the organic promoter must meet certain requirements related to its ability to bond metal ions. Promoters of this invention are compounds whose fully or partially deprotonated forms can serve as a hexadentate, octadentate, or decadentate chelating, binucleating ligand for two similar or different transition metal ions chosen from the list of essential metal ions, such that each metal ion may be bonded to three, four, or five heteroatom sites of the ligand. Preferably, the promoter is structured such that there can be five-coordinate binding by each metal atom; i.e., each metal binds to five heteroatom sites of the ligand.

The heteroatom sites may be nitrogen, oxygen, sulfur, phosphorus, or arsenic atoms as farther described below. The ligand further comprises at least one amido or one imino functionality; in a preferred embodiment, the ligand comprises four symmetrically distributed amido groups (e.g., tetraoxo tetraaza). The binucleating ligand can be acyclic or cyclic, but cyclic structures are preferred.

In preferred embodiments, the metal binding sites which fall between, and separate, the chelated metal ions are preferably bridging sites which can bind both metals in the binucleated system. Preferably, the bridging sites are chosen from hydroxyl, oxy, oxo, or thiol functionalities. Alternatively, the binding sites which fall between, and separate, the metal ions may comprise groups that bind only one metal, such as amino or pyridino sites, but such groups are not preferred in these positions. Binding the metal ions is accompanied by loss of amide, hydroxyl or thiolic protons. As a result, dipositive metal ions, for example, form neutral complexes when bound to the preferred tetraamido-type ligands.

In one set of preferred embodiments, the ligand structure contains additional electron donating substituents beyond the one required amido or imino group. This may be in the form, for example, of multiple amido groups (e.g., tetraamido), or other suitable electron donating groups.

In other preferred embodiments of the promoter, it is preferable to avoid the presence of tertiary hydrogen atoms; however, they may be present in the promoters useful in the present invention.

In certain embodiments, the ligand may be partially or fully fluorinated or otherwise halogenated to impart oxidative stability to the structure. When present, such halogen atoms are preferably substituted for hydrogen atoms on the spacer groups, though they may be present on other sites as well.

The ligand structures may be cyclic or acyclic, chiral or achiral, and symmetric or asymmetric. While the promoters useful in the catalysts of the present invention are not limited by requirements regarding flexibility or topology, it is understood that cavity size, spacer group size and flexibility is such that, preferably, two metal ions, optionally of different atom types and/or different oxidation states, can be accommodated in such a way so as to allow for oxygen binding by the oxidant to one or both metal ions (e.g., superoxo or $\mu$-peroxo binding).

It is understood that some or all of the additional features described herein may be present in various promoters used in forming the catalysts. The promoter has been described herein as a ligand bound to metal ions. However, as noted above, the promoter may or may not be bound to the metals when comprising part of the overall catalyst used in the process of the invention.

An example of a suitable compound for use as a promoter is the 26-membered octaaza macrocycle: 3, 6, 9, 17, 20, 23, 29, 30-octaazatricyclo[23.3.1.1.$^{11,15}$]triaconta-1(29), 11, 13, 15(30), 25, 27-hexaene-2, 10, 16, 24-tetraone, abbreviated TOBP, the structural formula for which is shown below (Formula 1), and which was first described in M. Kodama, T. Koike, and E. Kimura, *Bull. Chem. Soc. Japan* (1995) 68, 1627, which disclosure is hereby incorporated by reference herein.

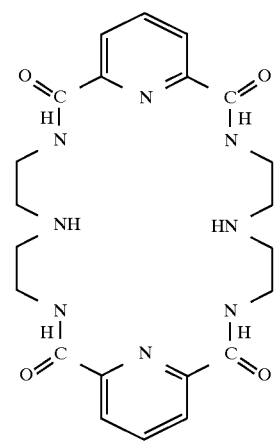

Formula 1

Several previously unknown metal complexes of TOBP were prepared in our laboratories. Some of these have utility as catalysts for aromatic ammination once supported and used in the manner of this invention. An example of such complexes is [Co(I), Pd(II) (TOBP)]. This product was characterized by NMR, IR electrochemically, by TLC, and by positive ion FAB-MS which showed the major peak at m/z=630 (assigned to M+1).

Another compound which is suitable for use as a promoter is the PROPALD structure. For example, the complex [VO (2+), Co(2+)(propald)(OAc)(H$_2$O)$_2$]$^+$, the structure of which is shown below (Formula 2), was prepared. The positive ion FAB-MS showed the highest mass peak at m/z=587 (assigned to M+2).

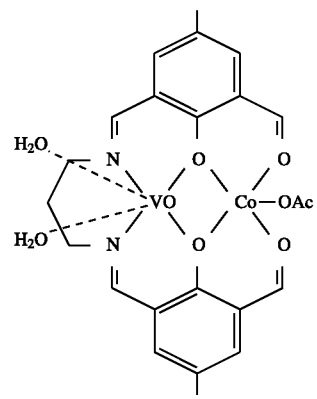

Formula 2

Many other binuclear complexes with ligands fitting the definition of promoters of this invention were prepared and characterized. For example, another suitable promoter structure, which is a novel composition of matter, is abbreviated EBPA. This structure features larger spacer groups than TOBP which results in increased flexibility to accommodate different size metal ions, each in 4-coordinate fashion. EBPA has the structure shown below (Formula 3).

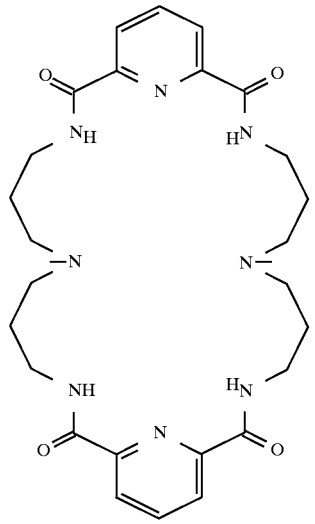

Formula 3

Another compound useful as a promoter in the catalysts of the present invention is abbreviated IATD and shown below (Formula 4).

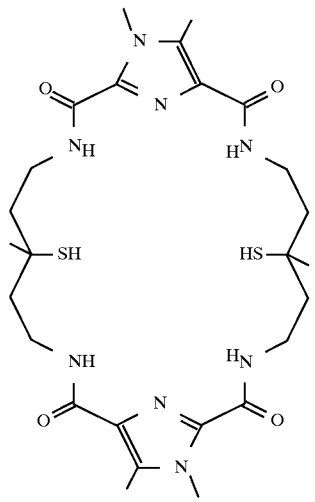

Formula 4

According to the structure proposed for IATD, thiol groups and amido groups can lose hydrogens when binding metal ions; also, thiolic sulfur atoms act as bridging atoms each capable of simultaneously binding two metals. Electron donating methyl substituents on each thiol-bound carbon atom replace an otherwise tertiary hydrogen atom.

Yet another suitable promoter structure is designated TANSIC and is drawn below (Formula 5):

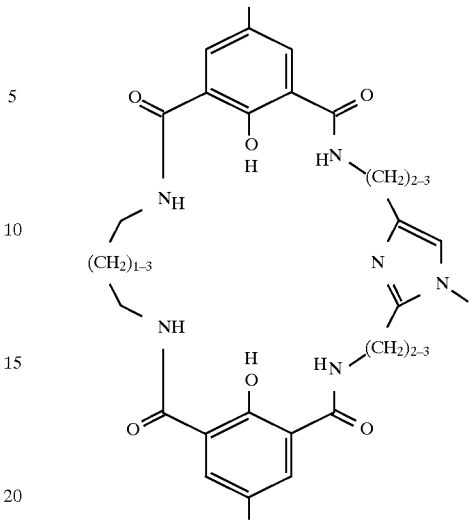

Formula 5

This structure is non symmetrical and features the capability of losing up to 6 protons to form neutral compounds with two tripositive metal ions or with a dipositive and tetrapositive metal ion. One metal could exist as a 4-coordinate complex and the other as a 5-coordinate complex with deprotonated forms of this ligand. Several variants of this structure are possible. For example, without limiting the scope TANSIC structures suitable for use in the present invention, there may be varying numbers of methylene spacer groups, varying number and types of substituents on the phenolic and/or imidazolic rings, and varying degrees of halogenation of the alkyl spacer groups. Protonated forms of the TANSIC structure are also useful as promoters.

The binuclear ligand CYPHIC also meets the criteria for a promoter for the purposes of the present invention. The structure of this ligand as complexed in the form of [Cu, $VO^{2+}$(CYPHIC)(OAc)($H_2O$)$_2$] is shown in Formula 6 below. During the synthesis of this complex, the protonated ligand $H_2$CYPHIC was not isolated.

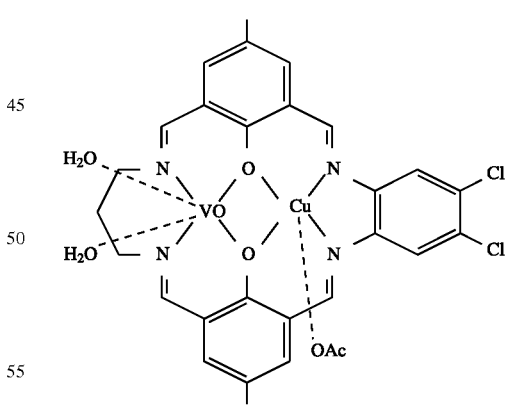

Formula 6

Catalyst Preparation

The catalysts described above may be prepared by synthesis of metal complexes comprising the promoter compounds as ligands bound to the metal(s), followed by their incorporation onto the surface of an appropriate support within prescribed loading ranges, followed by drying. Alternatively, the catalysts may be prepared by separately incorporating metal ions and organic promoter compounds onto suitable supports in two independent steps. Since some of the preformed complexes are insoluble in common laboratory solvents, when using incipient wetness loading techniques, for example, separate impregnation of each of a metal salt solution and of an organic promoter solution can be a preferred preparative method. Addition of the promoter compound to the support followed by addition of the essential metal component is a generally preferred order of addition, though not essential.

A stoichiometric amount of a base may optionally be added in some cases to enhance deprotonation of the promoter compounds such that metal ions may more readily bind; however, care must be taken to ensure that base addition will not prematurely precipitate metal salts. In some cases, the promoter species cannot be isolated as a discrete compound that is not bound to a metal. It is understood that multiple metals and multiple organic promoters can be added onto the same support particles or shaped bodies within the scope of this invention. Other compounds in addition to promoter compounds may optionally be added to serve as additional ligands or modifiers.

EXAMPLES

The following examples illustrate preparation of catalyst or catalyst components:

Example 1

A sample of the catalyst $VO^{2+}$/TOBP/$TiO_2$ was prepared as follows. A sample of titania (anatase titania) [14.16 g] that had been ground and sieved to 18/35 mesh was warmed in air on a hot plate to about 90° C. TOBP [0.54 g] was dissolved into ethanol and impregnated onto the titania with mixing of the solid; additional ethanol was added to bring the solid to incipient wetness. The solid was dried on a hot plate while exposed to air. An aqueous solution of $VOSO_4 \cdot 3H_2O$ [0.78 g] was prepared and the solid impregnated with it, followed by drying. A second solution of TOBP [0.26 g] in ethanol was prepared and the solid impregnated with it and air dried. The sample was then dried in a vacuum oven at about 190° C. under full vacuum for 3 hours. This solid, containing a nominal 1.2 wt. % V, was used as a catalyst with no further treatment.

Example 2

A second sample of TOBP-containing catalyst was prepared as above except only one dose of TOBP was added, and the sample washed with water followed by ethanol after impregnation to remove unreacted TOBP, vanadium salts, and sulfuric acid byproduct. The sample was dried as above prior to use.

Example 3

A third catalyst was prepared as follows: A sample of $[Cu^1(VO^{2+})(CYPHIC)(OAc)(H_2O)_2]$ which had been previously synthesized and characterized was dissolved in acetonitrile/ethanol, and the solution impregnated at room temperature onto 18/35 mesh anatase titania that had been previously dried at 130° C. to give a nominal loading of 4 wt. % complex. Acetonitrile was evaporated by stirring the sample with a spatula in a Petri dish on a hot plate in a fume hood. The sample was then placed in a vacuum oven while still moist and heated to about 140° C. under vacuum for about 2 hours.

Example 4

A fourth catalyst sample, $Cu^+$/TOBP/SK-500 zeolite, was prepared as follows: 14.07 g of a commercial sample of 1/16 inch extrudates of SK-500 zeolite were boiled repeatedly in distilled water following by decanting to remove soluble sodium silicate impurities. Copper(I)acetate [2.49 g] was dissolved into ca. 80 mL of dilute acetic acid with stirring and heating to give a blue solution. The copper solution was added to the washed zeolite and the mixture boiled for 10 minutes. After decanting, the solid was washed four times with boiling distilled, deionized water and hot acetonitrile. TOBP [0.13 g] solid was sprinkled over the solid zeolite and the mass just covered with ethanol. After thoroughly mixing with a spatula while heating on a hot plate, the solid was washed with additional ethanol and acetonitrile to remove unreacted TOBP. The sample was dried in a Petri dish on a hot plate, followed by further drying at 165° C. in a vacuum oven for 1 hour.

Example 5

The promoter ligand EBPA was synthesized for the first time by the following method. An ethanolic solution (400 mL) of dimethyl-2,6-pyridinecarboxylate [20 mmol, 3.9 g] and dipropylenetriamine [20 mmol, redistilled] was prepared and allowed to reflux for 4 days. After the reflux period, the solvent was evaporated to give an amber oil. Redissolution in ethanol or trichloromethane, followed by cooling in a refrigerator, failed to produced a precipitate. Extraction of the oil with water at room temperature, followed by rotary evaporation of the separated water layer, produced 3.1 g of an amber solid [12.5% yield prior to purification]. The solid showed a clean m/z =553 signal in the FAB positive ion mass spectrum and a single component besides the original spot in normal phase TLC using $CHCl_3$, as the mobile phase with a Rf of 0.21. An attempt to recrystallize the solid from hot ethanol failed to produce crystals; hence, the solid was used without further purification in subsequent tests.

Example 6

The promoter $H_2$PROPALD, as a free ligand (1,3-diaminopropane-4-methyl-2,6-diformylphenol), was synthesized as follows. 2,6 diformylcresol [14.3 mmol, 2.34 g] was dissolved in dry ethanol and allowed to condense with propylenediamine [7.15 mmol, 0.53 g, redistilled] under reflux conditions. Mass spectroscopy showed the major peak to be m/e=366 and a smaller peak at m/e=338; Proton NMR (CDCl3) indicated peaks at 14.24, 10.44, 8.36, 7.43, 7.27, 3.74, 2.27, and 2.12 ppm.

Example 7

The CYPHIC promoter [Co(II),Cu(I)(cyphic)](OAc), as mixed isomers, was synthesized as follows. Dihydrogen PROPALD [4.3 mmol, 1.576 g] was dissolved into methanol. Cobalt(II) acetate [4.3 mmol, 1.07 g] and copper(I) acetate [4.3 mmol, 0.527 g] were dissolved into another aliquot of methanol. The methanol solutions were combined and stirred for 4 hours, then 4,5-dichlorophenylenediamine [4.3 mmol, 0.761 g] added to the solution with vigorous stirring. The resulting solution was refluxed overnight then cooled and evaporated to dryness. The solid was recrystallized from hot water. FAB-MS indicated the major m/e peak to be 628 (M+2 of [Co(II),Cu(I)(cyphic)]+, rel intensity= 100%); 626 (90%); 630 (37%) and indicated small impurity peaks at 633 and 780 from which it was estimated that impurity level was about 12%.

Example 8

The promoter [Cu,Co(cyphic)](OAc), as a single positional isomer, was synthesized as follows. Preformed and isolated [Cu(propald)] complex [0.6 mmol, 0.257 g] was combined with cobalt (II) acetate [0.6 mmol, 0.149 g] and stirred for 1 hour at room temperature in methanol. Dichlorophenylenediamine [0.6 mmol, 0.106 g] was added and the solution refluxed overnight. Upon cooling in a refrigerator, 330 mg of a solid were isolated. FAB-MS (positive ion) indicated that the proper compound had been prepared; No quantitative analysis was performed to determine the isomer purity, but TLC in $CH_2Cl_2$ showed only one spot on silica-gel plates.

Example 9

The promoter [Co(II),Pd(II)(TOBP)] was synthesized as follows. $H_4$TOBP free ligand [1 mmol, 0.47 g] was dissolved in ethanol and an ethanolic solution of cobalt acetate added [1 mmol, 0.25 g]. The solution was stirred 1 hour, then palladium acetate added [0.224, 1 mmol] which had been predissolved in a minimum of ethanol. The ethanol volume was brought up to 250 mL and the solution refluxed with stirring for 2 hours. An initially formed precipitate was filtered off, and the supernatant solution evaporated to dryness yielding the desired product. FAB-MS (positive ion) indicated a clean major peak at m/e=630 (M+1), [No peak at 469 was evident M+1 of $H_4$TOBP)]; FTIR analysis indicated the CO stretch to have moved from 1669 cm-1 in free $H_4$TOBP to 1596 cm-1 in the heterobinuclear complex.

Example 10

The synthesis of promoter IATD may be carried out in a manner similar to that described for EBPA using the precursors, dimethyl-1-methyl-2,4-imidazoledicarboxylate and 3-methyl-3-mercapto-pentane-1,5-diamine, which in turn may be prepared by standard synthetic methods. Modifications to the procedure involve the use of appropriate protecting groups to prevent the destruction of sensitive functional groups.

Examples 11–14

The following examples, detailed in Table I below, illustrate use of the catalysts for the oxidative ammination of benzene. The last two columns of the table above illustrate the requirement for the nitro ligand in the Pd-based catalysts of this invention ammonia and oxidant under suitable reaction conditions in the presence of a catalyst comprising:

(a) a support;
(b) transition metal selected from the group consisting of vanadium, niobium, copper, palladium, nickel and silver, or combinations thereof; and
(c) a promoter comprising a mononuclear or binuclear ligand comprising at least one nitro or nitroso group.

2. The process of claim 1 wherein said ligand comprises at least one nitro or nitroso group.

3. The process of claim 2 wherein said ligand further comprises at least one amido group.

4. The process of claim 2 wherein said support is selected from a group consisting of metal oxides, molecular sieves, zeolites and clays.

5. The process of claim 4 wherein said support comprises silica.

6. The process of claim 2 wherein said catalyst further comprises about 1 to about 70 weight percent barium compounds.

7. The process according to claim 6 wherein said barium compounds comprise barium peroxide.

8. The process of claim 2 wherein said transition metal comprises palladium or nickel or combinations thereof.

9. The process of claim 8 wherein said transition metal comprises palladium.

10. The process of claim 8 wherein said transition metal comprises nickel.

11. A process for catalytic ammination of aromatic hydrocarbons comprising contacting aromatic feedstock with oxidant comprising molecular oxygen under suitable reaction conditions in the presence of a catalyst comprising:

(a) a support;
(b) transition metal selected from the group consisting of vanadium, niobium, copper, palladium, nickel and silver, or combinations thereof; and
(c) a promoter comprising a multidentate chelating, binucleating ligand (i) comprising heteroatom sites

TABLE I

OXIDATIVE AMMINATION OF BENZENE TO ANILINE

| Example | 11 | 12 | 13 | 14 |
| --- | --- | --- | --- | --- |
| Catalyst Type | V,CU/TOBP/TIO$_2$ | VOSO$_4$/TOBP/TIO2 | Pd(NH$_3$)$_2$ (NO$_2$)$_2$ /SiO$_2$ | Pd(NH$_3$)$_2$ Cl$_2$/SiO$_2$ |
| Active Metal | V, Cu | V | Pd | Pd |
| Wt/% Active Metal | 3% | 3/3% | 12% | 12% |
| Promoter | TOBP | TOBP | none | none |
| T(°C.) | 250 | 265 | 280 | 240 |
| P(psig) | 840 | 841 | 830 | 832 |
| time on-stream (h) | 2 | 1 | 3–10 | 6 |
| FEED | | | | |
| benzene | yes | yes | 32 mg/min | 32 mg/min |
| water | no | no | 0 | 0 |
| NH$_3$ (anhyd) | yes | no | 0 | 0 |
| NH$_4$OH (aq) | no | yes | 49 mg/min | 49 mg/min |
| air | yes | yes | 121 mL NTP/min | 120 mL NTP/min |
| Conversion (mol %) | 14 | 0.4 | 0.12 | <0.05 |
| carbon sel aniline | ratio rel. amt.: 1 * | 1.1 | 18–29 | 0 |
| carbon sel phenol | ratio rel. amt.: 12 * | 11.8 | 14.5–23 | 59 |
| carbon-sel biphenyl | ratio rel. amt.: 41 * | | 30.1–48 | 21.6 |
| carbon sel CO$_2$ | major product | 15.3 | 37–2 | <1 |
| reactor type | packed bed | RM-CSTR | packed bed | packed bed |

* The amounts of products (aniline:phenol:biphenyl) in Example 7 are expressed as relative amounts because the amount of CO$_2$ produced was not quantified in that run.

What is claimed is:

1. A process for catalytic ammination of aromatic hydrocarbons comprising contacting aromatic feedstock with comprising nitrogen, oxygen, sulfur, phosphorus or arsenic atoms or combinations thereof, and (ii) comprising at least one amido or imino group.

12. The process of claim 11 wherein said support is selected from a group consisting of metal oxides, molecular sieves, zeolites and clays.

13. The process of claim 12 wherein said metal oxides are selected from the group consisting of pure metal oxides, mixed metal oxides and doped metal oxides.

14. The process of claim 12 wherein said molecular sieves are selected from the group consisting of titanium framework-substituted and vanadium framework-substituted molecular sieves.

15. The process of claim 12 wherein said clays are selected from the group consisting of intercalated clays and pillared clays.

16. The process of claim 12 wherein said support comprises compounds comprising titanium, vanadium, magnesium or aluminum or combinations thereof.

17. The process of claim 16 wherein said support comprises titania.

18. The process of claim 11 wherein said catalyst further comprises ions of one or more additional metals.

19. The process of claim 18 wherein said additional metals comprise transition metals.

20. The process of claim 19 wherein said additional metals are selected from the group consisting of cobalt, iron, manganese, titanium, ruthenium, molybdenum, tungsten, tantalum and gadolinium, or combinations thereof.

21. The process of claim 11 wherein said ligand is capable of binding two atoms of said transition metal to three to five heteroatom sites of said ligand.

22. The process of claim 21 wherein said ligand is capable of binding said atoms of transition metal to five heteroatom sites of said ligand.

23. The process of claim 11 wherein said ligand comprises four symmetrical amido groups.

24. The process of claim 11 wherein said ligand is selected from the group consisting of TOBP, PROPALD, EBPA, IATD, TANSIC and CYPHIC, or metal coordinating complexes thereof.

25. The process of claim 11 wherein said catalyst comprises more than one promoter.

26. The process of claim 1 or 11 wherein said reaction conditions comprise a temperature in a range from 100° to 450° C. and a pressure greater than 0 psig.

27. The process of claim 26 wherein said temperature is in a range from 250° to 320° C.

28. The process of claim 26 wherein said pressure is in a range from 500 to 900 psig.

29. The process of claim 1 or 11 wherein said aromatic feedstock comprises unsubstituted or substituted aromatic compounds.

30. The process of claim 29 wherein said aromatic feedstock comprises benzene or naphthalene.

31. The process of claim 30 wherein said aromatic feedstock comprises benzene.

32. The process of claim 29 wherein said aromatic feedstock comprises substituted aromatic compounds comprising one or more substituents selected from the group consisting of alkyl groups, alkoxy groups, halogen atoms, amino groups, alkylamino groups, carboxyl groups, nitro groups, nitroso groups, sulfo groups, sulfone groups, and sulfoxy groups, or combinations thereof.

* * * * *